(12) United States Patent
Mantelmacher

(10) Patent No.: US 9,492,292 B2
(45) Date of Patent: Nov. 15, 2016

(54) PROSTHETIC SOCKET CENTERING BLOCK

(71) Applicant: H. Lee Mantelmacher, Owings Mills, MD (US)

(72) Inventor: H. Lee Mantelmacher, Owings Mills, MD (US)

( * ) Notice: Subject to any disclaimer, the term of this patent is extended or adjusted under 35 U.S.C. 154(b) by 96 days.

(21) Appl. No.: 14/373,059

(22) PCT Filed: Dec. 14, 2012

(86) PCT No.: PCT/US2012/069768
§ 371 (c)(1),
(2) Date: Jul. 18, 2014

(87) PCT Pub. No.: WO2013/090733
PCT Pub. Date: Jun. 20, 2013

(65) Prior Publication Data
US 2015/0005897 A1    Jan. 1, 2015

Related U.S. Application Data

(60) Provisional application No. 61/570,584, filed on Dec. 14, 2011.

(51) Int. Cl.
| | | |
|---|---|---|
| A61F 2/78 | (2006.01) | |
| A61F 2/80 | (2006.01) | |
| A61F 2/60 | (2006.01) | |
| A61F 2/76 | (2006.01) | |
| A61F 2/50 | (2006.01) | |

(52) U.S. Cl.
CPC . *A61F 2/80* (2013.01); *A61F 2/60* (2013.01); *A61F 2/76* (2013.01); *A61F 2002/5018* (2013.01); *A61F 2002/5023* (2013.01); *A61F 2002/5083* (2013.01); *F04C 2270/0421* (2013.01)

(58) Field of Classification Search
CPC ............... A61F 2002/5018; A61F 2002/5021; A61F 2002/5023; A61F 2002/5083; A61F 2/76
USPC .......................................................... 623/38
See application file for complete search history.

(56) References Cited

U.S. PATENT DOCUMENTS

| | | | |
|---|---|---|---|
| 5,653,766 A | 8/1997 | Naser | |
| 6,645,253 B2 | 11/2003 | Caspers | |
| 6,793,682 B1 | 9/2004 | Mantelmacher | |
| 7,083,654 B2 * | 8/2006 | Helenberger | A61F 2/76 623/33 |
| 7,727,284 B2 * | 6/2010 | Warila | A61F 2/78 623/33 |
| 2003/0233151 A1 * | 12/2003 | Lund | A61F 2/78 623/36 |

* cited by examiner

*Primary Examiner* — Bruce E Snow
(74) *Attorney, Agent, or Firm* — Ober, Kaler, Grimes & Shriver; Royal W. Craig

(57) ABSTRACT

A prosthetic component centering block (10) for mounting and adjustably centering a socket to a prosthetic leg, and for establishing and maintaining proper flexion and offset there between. The centering block (10) comprises a solid member defined by an upper surface, lower surface, and surrounding sides. Both the upper surface and lower surface define an elongated geometric shape extending from a front end to a rear end, and the upper surface is inclined front-to-rear at a pre-determined flexion angle Φ relative to said lower surface.

19 Claims, 4 Drawing Sheets

PROSTHETIC SOCKET CENTERING BLOCK

BACKGROUND OF THE INVENTION

1. Field of the Invention

The present invention relates to prosthetics and, more particularly, to a prosthetic socket centering block to allow convenient mounting of prosthetic limbs for above-the-knee and below-the-knee amputation patients at selectable flexion angle and offset.

2. Description of the Background

There are a variety of different types of prosthetic devices for patients that have had either transfemoral (above-knee) or transtibial (below the knee) amputation. Typically, postoperative prosthetic devices for either type of amputation begins with a liner that is rolled onto the residual limb. The liner is a soft, stretchy material that acts as an interface with the prosthesis.

Once the liner is on, the residual limb then slides into a hard socket. This socket is specially made to fit and can be made out of a variety of materials.

The hard socket for a transfemoral prosthesis has a knee joint connected to it, and the more fluid and natural the movement of the knee the better. Transtibial prosthetics have no knee joint. In both cases (with or without a knee joint) there is typically an aluminum or carbon fiber tube to which a foot module is connected.

For example, U.S. Pat. No. 5,653,766 to Naser issued Aug. 5, 1997 shows a prosthetic device 20 having a generally cylindrical socket 24 with an opening for receiving an amputated limb. The socket 24 is closed at the other end, and is mounted on a bendable knee joint. Once the limb is properly received within the socket 24, straps 38 are adjusted so that a secure fit is achieved. The patient then is able to walk using the prosthetic device 20.

With all such transfemoral and/or transtibial prosthetics (above & below the knee), it is very important that the socket be securely fitted to the limb and secured in place. Stability is a common problem as many existing anchoring systems use a single attachment point to hold the residual limb in place, and this typically leads to extraneous pivoting, rotation and shift during ambulation. The prior art ICEX® Socket System uses a combination lanyard and pin kit as a docking and locking mechanism. The socket has a distal pin that docks with the prosthesis. A lanyard is connected to the liner through a slot in the bottom of the socket. The lanyard is pulled to allow the patient's residual limb, which is enclosed in the silicone liner, to be drawn into the socket by the lanyard. The lanyard is then anchored to the front of the socket.

There are also a number of "suspension" type sockets that eliminate the pin. U.S. Pat. No. 6,645,253 to Caspers issued Nov. 11, 2003 shows a suction system that employs a vacuum pump to impart suction to the liner, the vacuum pump doubling as a shock absorber for the artificial limb. Commercially, this is known as the Harmony® System which pulls air from the sealed socket and evacuates moisture (sweat) buildup. A nonporous polyurethane liner (not shown) is fitted over the residual limb and is inserted in the socket. A vacuum pump is attached via a connector block beneath the socket to create a vacuum force which is coupled by a tube to the liner, thereby evacuating air and sealing it to the residual limb. This provides a total-contact hypobaric suction equal weight distribution socket liner which tacks up to the skin of the residual limb and provides total contact with the limb.

U.S. Pat. No. 6,793,682 to the present inventor discloses a "Sure-fit Prosthetic Attachment System" (known commercially as the KISS® System) for transfemoral and/or transtibial prostheses, comprising a liner for enveloping an amputee limb. The liner has a strap attached at one end to a reinforcement plate that is sewn and/or bonded to the liner toward the top, and a buckle is attached to the other end of the strap and is suspended thereby from the liner. Another strap is fixedly attached to the bottom end of the liner. The anchoring system also includes a containment socket for seating the liner. The containment socket has a pair of slots there through at positions corresponding to the buckle and strap of the liner, respectively. To apply the anchoring system, the patient first applies the liner to his/her limb. The liner is then inserted into the socket with the fastening strap and buckle protruding out through the respective slots. The fastening strap is then threaded up through the buckle (running upward along the side of the socket) and is inserted there through. The patient pulls down on the strap, which works by pulley action to draw the liner down into the socket until the liner is securely seated in the socket. When fully seated, the fastening strap is secured to itself by Velcro®. The foregoing forms a suspension which holds the prosthesis on. Moreover, the fastening straps through slots absolutely prevent lateral shift as well as rotation. On the other hand, the patient need only readjust the Velcro® closure to adjust the position of the limb within the socket. Thus, if the limb changes position because of volume change and the distal migration of the limb into the socket, the prosthesis can easily be adjusted to compensate.

One of the primary concerns of prosthesis design and construction is that the device be lightweight and provide a comfortable fit to the residual limb, and it is extremely important to emulate a natural gait when in use. To provide the user with a comfortable and natural gait, it is of primary concern that the prosthesis be properly aligned so that its movement conforms to the shape and movement mechanics of the wearer's body. The goal is to duplicate the normal knee position and alignment. Taking the time to properly bench align a prosthesis contributes to a smooth, energy efficient gait pattern. A proper bench alignment controls knee flexion after heel strike, ensures smooth rollover with limited hyperextension, and controls "heel off" prior to initial contact on the other foot. Generally, a small degree of socket flexion (anterior tilt in the socket with respect to the foot) is desirable to assist better loading in the socket and help create a smoother gait pattern. Flexion in the socket positions the limb in a natural midstance position and helps reduce hyperextension tendencies during gait. As seen in FIG. 1, normal socket flexion should be set to a 5-7 degree angle, though it may vary in different situations when contractures are present (muscle contractures result from muscle imbalance problems associated with the prosthetic). In addition to socket flexion angle, the center of the foot should be offset from the knee joint. For this, the center of the foot is normally placed 30 mm in front of the alignment reference line and mounted with plantar flexion. Presently, more than normal (greater than 7 degree) offset and flexion angle are achieved with external-to-the-socket offset angled flexion plates, as seen in FIGS. 2 and 3, which are typically provided in a range of flexion angles (each fixed at a particular angle). The prosthetic pylon and knee are mounted at the offset rear of the plate, while the socket is mounted to a socket mounting block attached to the fore of the plate. Flexion plates which are external to the socket, however, add undue weight, bulk, instability, and cosmetic issues.

It would be more advantageous to provide a prosthetic socket mounting block that directly facilitates mounting of the prosthetic socket to the pylon and knee, simultaneously instilling the proper flexion angle and offset in order to construct and align the diagnostic prosthesis, while the offset and angle remains within the structure of the socket device.

SUMMARY OF THE INVENTION

It is, therefore, an object of the present invention to provide an inner-socket trans-femoral prosthetic component centering block for mounting and adjustably centering a socket to a prosthetic leg, and for establishing and maintaining proper flexion and offset there between.

It is another object to provide an internally-mounted socket centering block that serves as both an attachment block for the socket to the knee, as well as an angled and offset adapter to accommodate hip flexion and offset for proper alignment of the prosthesis.

In accordance with the above-described object, an unproved prosthetic component centering block is disclosed for mounting and adjustably centering a socket to a prosthetic leg, and for establishing and maintaining proper flexion and offset there between. The centering block comprises a solid member defined by an upper surface, lower surface, and surrounding sides. Both the upper surface and lower surface define an elongated geometric shape extending from a front end to a rear end, and the upper surface is inclined front-to-rear at a pre-determined flexion angle Φ relative to said lower surface. A recess is formed in the upper surface of the solid member for seating and centering a prosthetic liner within the attached socket, and a plurality of mounting holes are formed in the lower surface in a symmetric pattern positioned about the front end of said lower surface.

The above and other objects, features and advantages of the present invention will become readily apparent from the following detailed description thereof which is to be read in connection with the accompanying drawings.

BRIEF DESCRIPTION OF THE DRAWINGS

Other objects, features, and advantages of the present invention become more apparent from the following detailed description of the preferred embodiments and certain modifications thereof when taken together with the accompanying drawings in which.

DETAILED DESCRIPTION OF THE PREFERRED EMBODIMENTS

Reference will now be made in detail to preferred embodiments of the present invention, examples of which are, illustrated in the accompanying drawings. Wherever possible, the same reference numbers will be used throughout the drawings to refer to the same or like parts.

The present invention is a trans-femoral prosthetic centering block attachable within and between a socket and a prosthetic leg for imparting proper flexion and offset there between.

Figure 1:
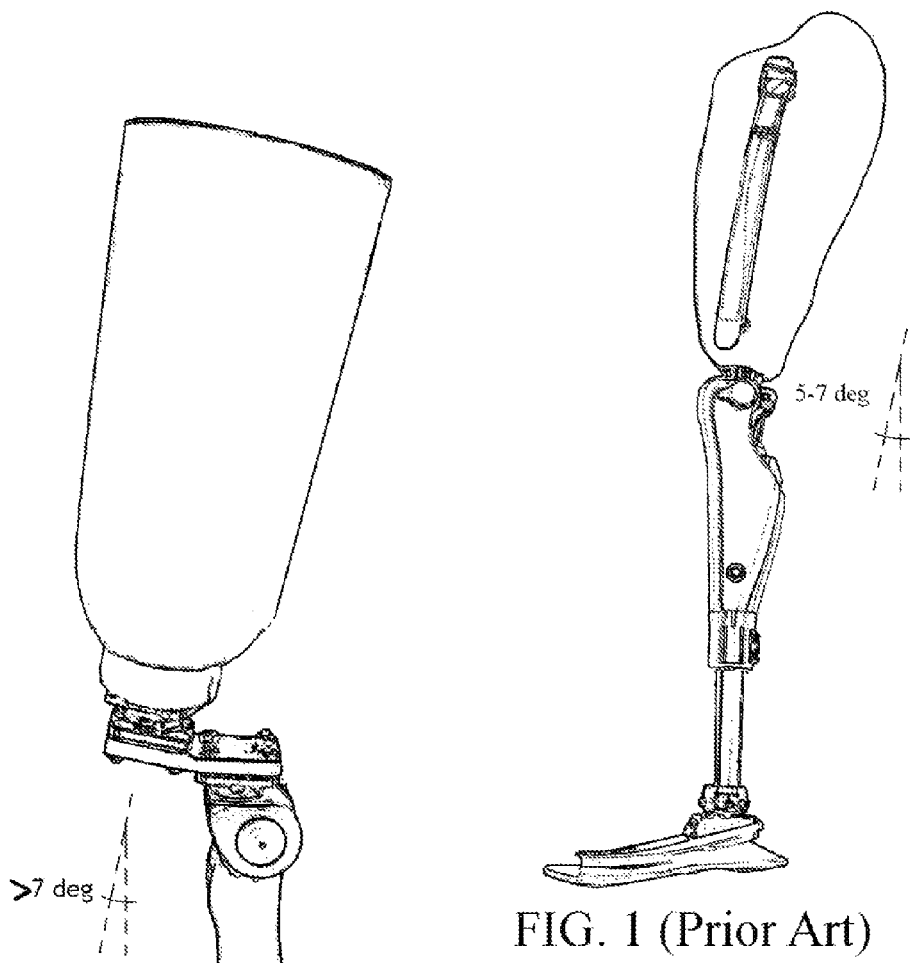
FIG. 1 is a perspective view illustrating normal 5-7 degree socket flexion with no offset, and no angled flexion plate.
Figure 2:
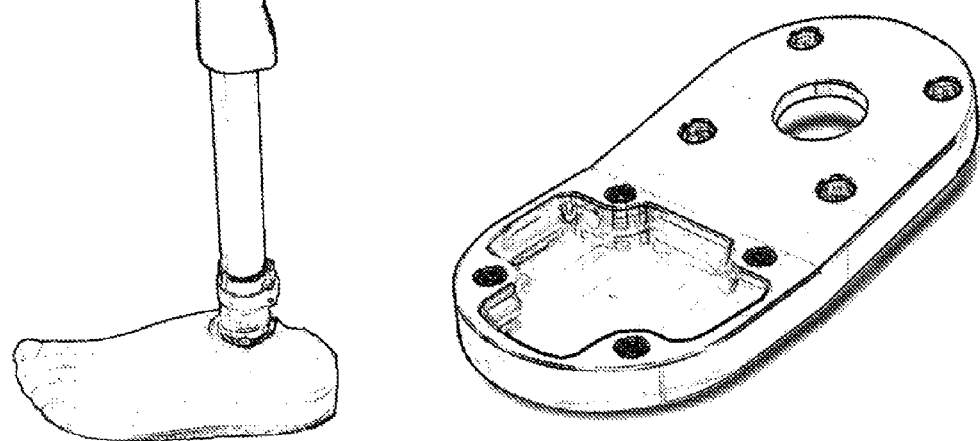
FIG. 2 is a diagrammatic perspective view illustrating greater-than-normal (>7 degree) socket flexion and offset from the knee joint, using a prior art angled flexion plate.
Figure 3:
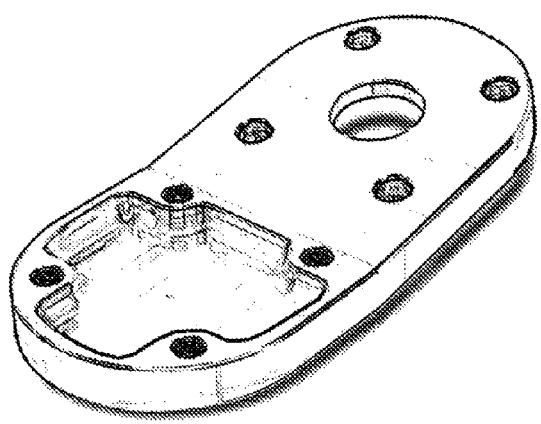
FIG. 3 is a perspective view of the prior art angled flexion plate of FIG. 1 which is adapted to be externally-attached to the socket.
Figure 4:
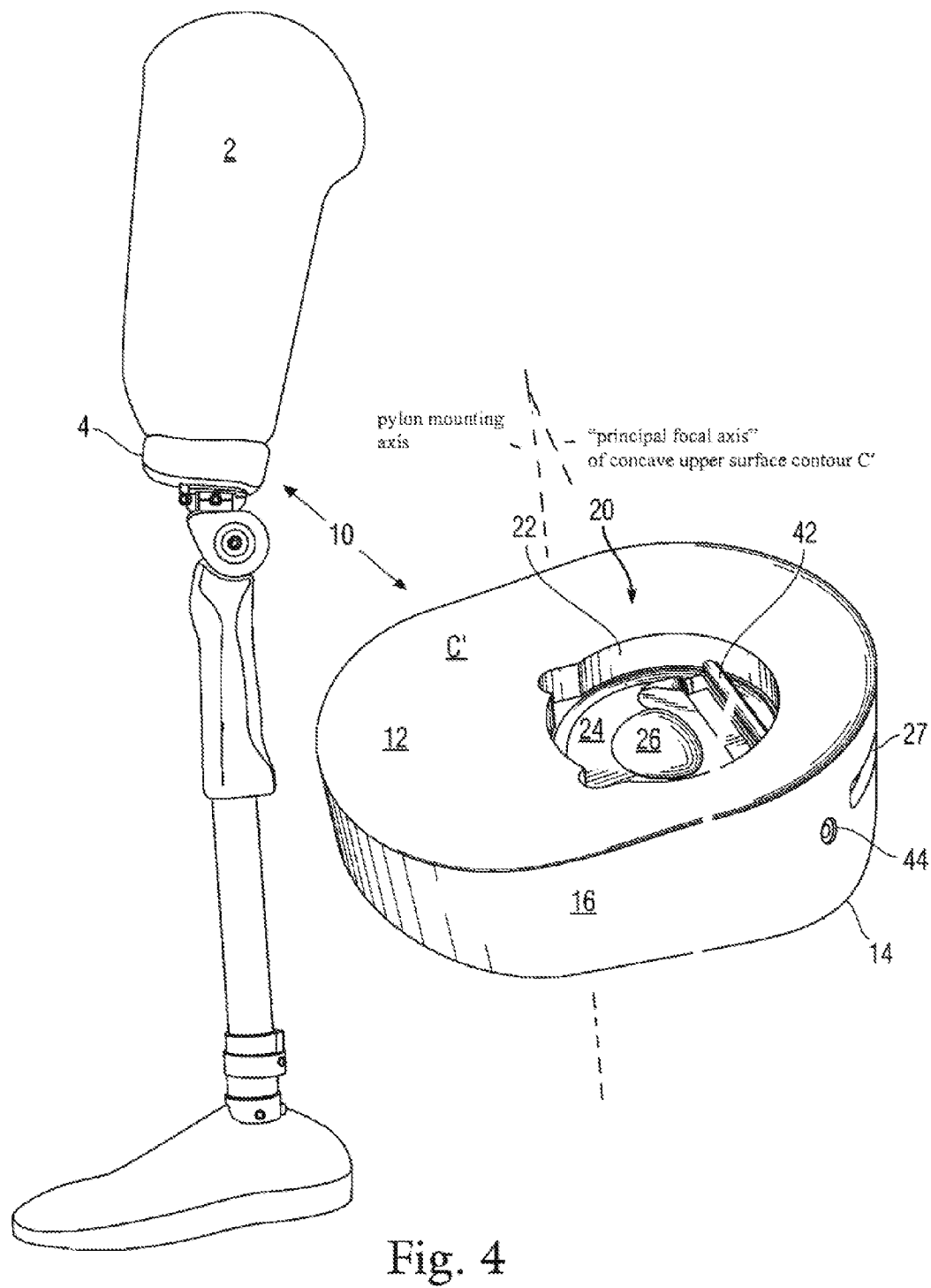
FIG. 4 is a top perspective view of an exemplary centering block 10 according to an embodiment of the present invention adapted for a suspension mount as seen in U.S. Pat. No. 6,793,682 to Mantelmacher (the KISS® System).
Figure 5:
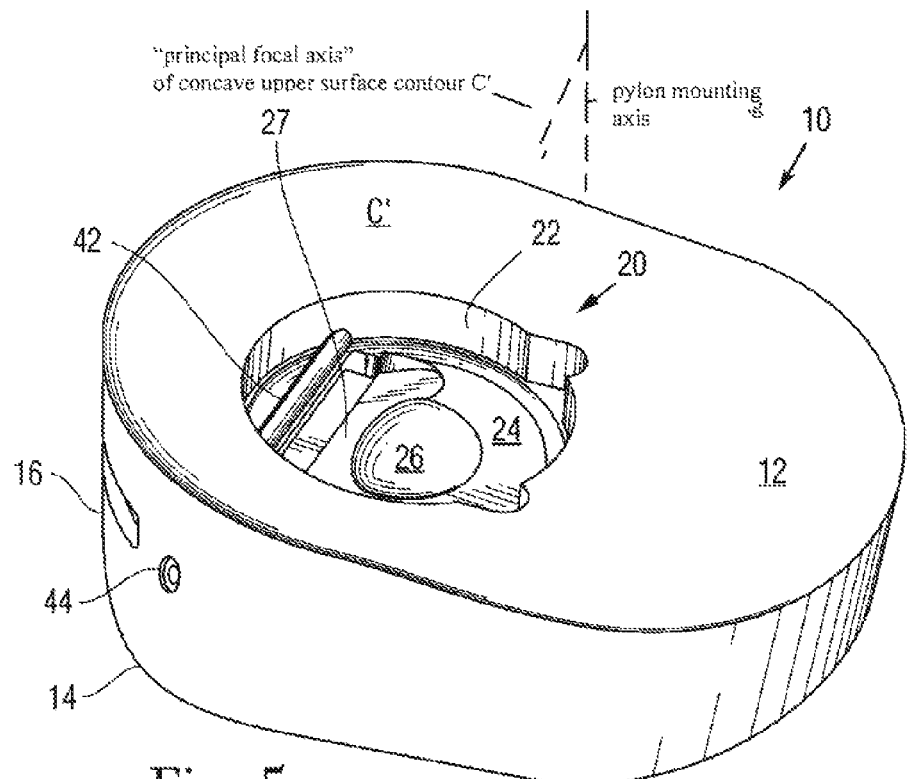
FIG. 5 is a top perspective view of the centering block 10 of FIG. 4.

With reference to FIG. 4 the prosthetic socket 2 may be cast, molded, laminated or otherwise formed of synthetic and durable material in accordance with known technology to define a unitary shell having a proximal open end entering a primary volume generally conforming to the residual limb of an amputee (not shown). The prosthetic socket 2 is rigid and is capable of carrying appropriate loads imposed by an ambulating amputee. The socket 2 can be shaped at its open end to accommodate a below the knee amputee or an above the knee amputee wearing an appropriate liner on their residual stump. Such liners are typically an elastomeric sock with low friction fabric outer cover. The socket 2 is provided with a chamber 4 molded into the distal end of the prosthetic socket 2 as an extension of the primary volume to accommodate the socket centering block 10 described below.

FIGS. 4-7 show the centering block 10 according to an embodiment of the present invention adapted for a suspension mount as per U.S. Pat. No. 6,793,682 to Mantelmacher (the KISS® System). Block 10 generally comprises a solid member formed of a suitable structurally-rugged material to define a unitary block having an upper face 12, lower surface 14 and surrounding sides 16. The upper surface 12 and lower surface 14 define two-dimensional geometric shapes. In the illustrated embodiment the preferred geometric shape of both upper surface 12 and lower surfaces 14 are eccentric oval, bounded at each end by spaced geometric circles of slightly different sizes. The block 10 is elongated lengthwise such that its length exceeds the transverse diameter of both circles, resulting in an oval with only one (lengthwise) axis of symmetry. The block 10 is surrounded by an outside wall that is approximately annular at each opposing end, and linear or slightly arcuate lengthwise, converging slightly from the larger geometric circle to the smaller. One skilled in the art should understand that although the foregoing is a preferred embodiment any suitable ovoid, oblong, or elliptical shape may suffice, including egg-shaped, and for purposes herein "oval" is herein broadly defined to include such shapes. The lower surface 14 is substantially flat about a majority of its area, including the area surrounding the focus of the first geometric circle. The upper surface is concave about a majority of its area, including the area surrounding the focus of the second circle.

Figure 7:
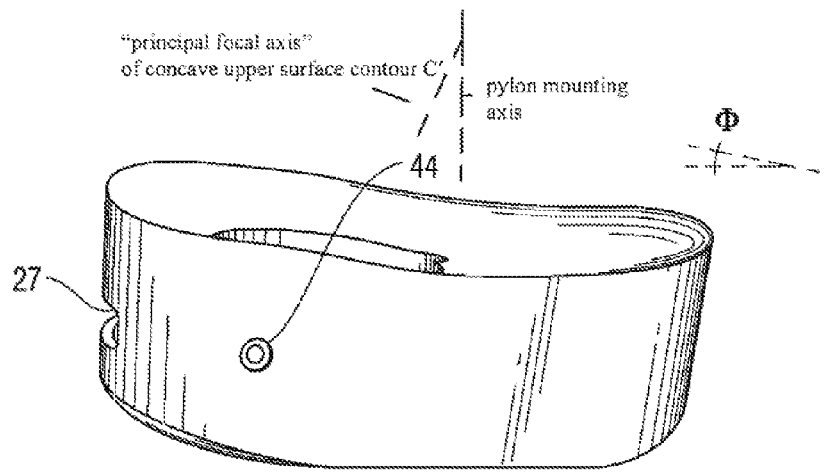
FIG. 7 is a side view of the centering block 10 of FIGS. 4-6.

The block 10 has a compound recess 20 in the upper surface 12 centered at the focus of the first geometric circle. The entire remainder of the upper surface 12 surrounding the recess 20 has a concave upper surface contour C' to match the contour of the distal area of the residual limb (which is covered by the gel liner), thereby improving seating and centering of the residual limb against the block 10 internally of the socket. More specifically, the concave upper surface contour C' is configured to seat the residual limb against the block 10 centered at the foci of the front geometric circle (directly overhead the compound recess 20), and to seat it in such a way as to impose the desired socket flexion angle Φ. For this, the prosthetic pylon, when attached to the lower surface of block 10 and protruding perpendicularly from the center focus of the second geometric circle, is canted at a slight angle Φ relative to the center-axis of the socket 10. The angle Φ is preferably within a range of from 2-20 degrees, even more preferably within a range of from 6-12 degrees, and is most preferably a 12 degree angle offset from horizontal. The foregoing flexion angle Φ can be accomplished by a slightly-angled orientation of the concave upper surface contour C' of block 10, or alternatively by generally inclining the upper surface 12 relative to the lower surface 14, or by a combination of the two. FIG. 7 shows how the shallow front-to-back angle Φ can be attained with an upper surface 12 that is inclined such that at rear it is offset by approximately 1" and progressively more so toward the rear running to 1.5", this overall incline imparting socket flexion angle.

The recess 20 includes a cylindrical section defined by a flat floor 24 and surrounding cylindrical walls 22. Floor 24 sits at an elevation that is approximately one third the thickness of the block 10, and the cylindrical recess 20 occupies another third. The cylindrical recess 20 opens to the concave upper surface contour C' which flares outward across a majority of the upper surface 12. The entire block 10 is preferably constructed of aluminum, Delrin® or other durable material and has a minimum thickness of approximately 20 mm (¾ inch) or as necessary to achieve a sufficiently rigid block of the selected material.

The recess 20 has a pronounced deeper portion 26 in the center of floor 24 for seating the head of a screw typically used for attaching an attachment strap. The floor 24 and recess 26 cut away to a slot 27 which continues sidelong out through the front sidewall 16 of the centering block 10 to pass the fastening strap from inside block 10 outside and back around for attachment elsewhere, such as to a mating strap coming from the liner. Note that the exit slot 27 may have rounded corners to avoid abrasion of the strap and to improve aesthetics, and two square-corners may be formed in the cylindrical recess 20 to accommodate the corners of the attachment strap which comes in inserted through slot 27 and is distally secured by a screw in deeper portion 26.

Figure 6:
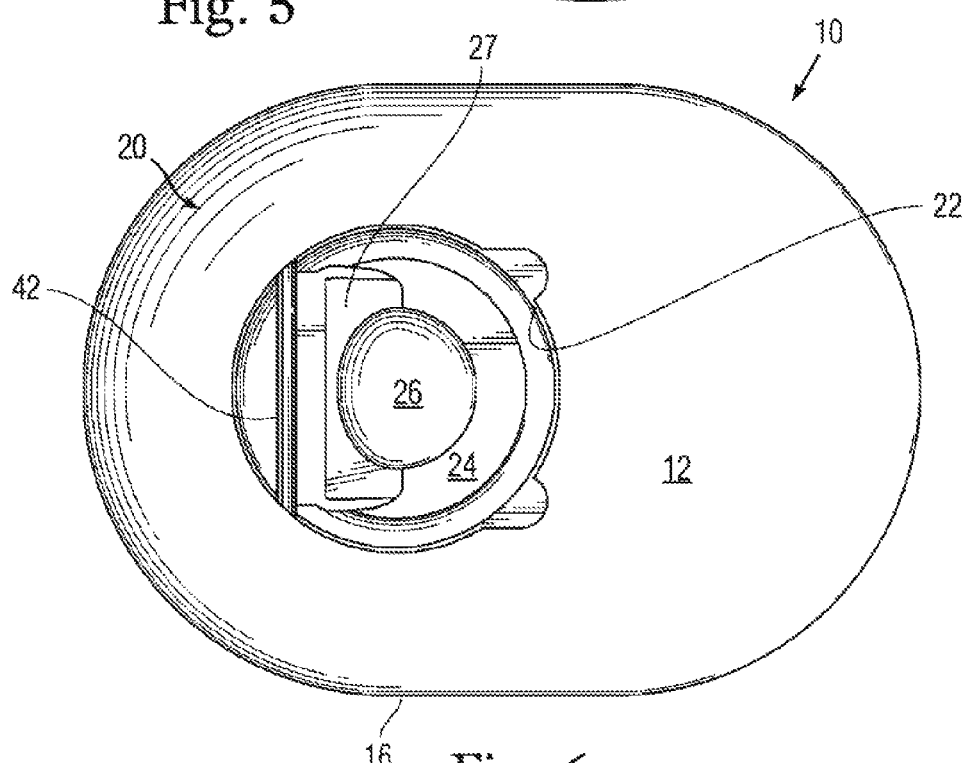
FIG. 6 is atop view of the centering block 10 of FIGS. 4-5.

As best seen in FIG. 6, a bearing pin 42 is inserted into the centering block 10 through a sidelong access port 44, and is suspended just overhead the slot 27 to serve as roller for easier frictionless insertion of an attachment strap through slot 27.

One skilled in the art should understand that the recess 20 dimensions and configuration may be altered as desired to accommodate other transfemoral and/or transtibial prosthetic mounting systems such as the ICEX® Socket System or otherwise.

Figure 8:
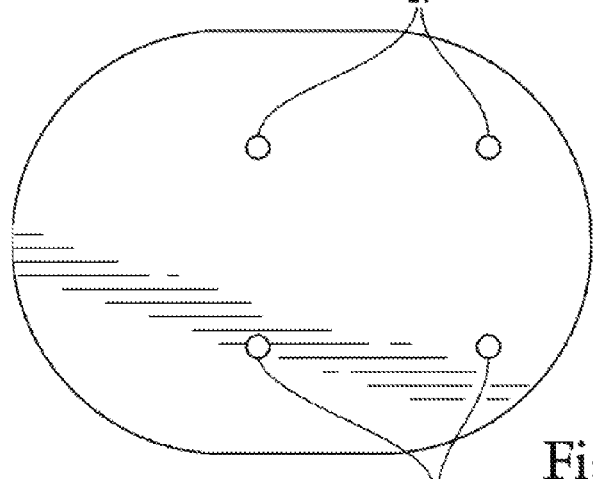
FIG. 8 is a bottom view of the centering block 10 of FIGS. 4-7.

As seen in FIG. 8, four (4) through-bores 37 are formed in a square pattern into the bottom of the centering block 10 along the flat portion to allow screw-attachment into the base of the bendable knee joint (transfemoral) or the base of the shaft (transtibial), either of which are typically attached directly beneath the centering block 10.

Figure 9:
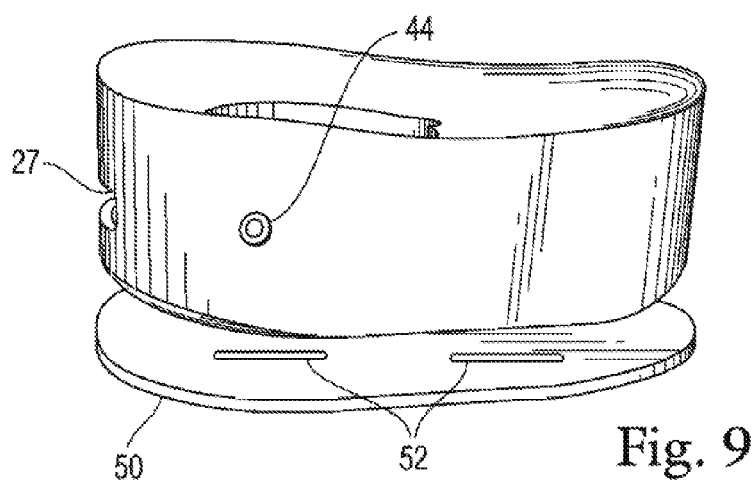
FIG. 9 is a side view of a centering block 10 with optional slide plate 50.

FIG. 9 illustrates an optional slide plate 50 which allows adjustment of the amount of lateral offset. The slide plate 50 is a flat plate that conforms to the dimensions of the centering block 10 and is defined by four slots 52 for passing screws into the through-bores 37 (FIG. 8). This allows separate screw-attachment of slide plate 50 into the base of the bendable knee joint (transfemoral) or the base of the shaft (transtibial), and then screw attachment of the slide plate 50 to the centering block 10 at any selectable offset along slots 52.

If desired, the top of slide plate 50 and bottom of centering block 10 can be made with conforming arcuate surfaces so that the cant or flexion the centering block 10 can be adjusted and set by similar adjustment of slide plate 50 to the centering block 10 at any selectable offset and angle along slots 52.

The internally-mounted block 10 seated within the chamber 4 of the socket 2 serves as both an attachment block for the socket 2 to the knee, as well as an angled and offset adapter to accommodate hip flexion and offset for proper alignment of the prosthesis. It allows bench-mounting and adjustable centering of the socket 2 to a prosthetic leg and securely establishes and maintains proper flexion and offset there between.

It should now be apparent that the above-described centering block 10 facilitates direct-mounting of a prosthetic socket to a prosthetic limb, and instills the proper flexion angle and offset in order to construct and align the prosthesis.

INDUSTRIAL APPLICABILITY

It is extremely important for a prosthetic leg to provide the user with a comfortable and natural gait, and this requires proper and precise alignment. Generally, a small degree of socket flexion (anterior tilt in the socket with respect to the foot) is desirable, though flexion may vary in different situations. It is also desirable to offset the foot from the knee joint. Presently, offset and flexion angle are achieved with external-to-the-socket offset angled flexion plates which add undue weight, bulk, and instability, and cosmetic issues. There would be great industrial applicability in a prosthetic socket mounting block that directly facilitates mounting of the prosthetic socket to the pylon and knee, simultaneously instilling the proper flexion angle and offset in order to construct and align the diagnostic prosthesis, while the offset and angle remains within the structure of the socket device.

I claim:

1. In combination with a prosthetic leg including a hard socket for receiving a stump of a residual limb covered by a prosthetic liner, a foot attached beneath said socket, and a pylon between said socket and foot, said socket being defined by a unitary hard shell having a proximal open end, a primary volume, a distal end, and a chamber at said distal end defining a distal volume, an improvement comprising:

a socket centering block seated in the chamber at the distal end of said socket for mounting and centering said socket to said pylon and establishing and maintaining a proper flexion angle and offset there between, said socket centering block consisting of a solid monolithic oval member defined by an upper surface, a lower surface having a flat area with plurality of mounting holes formed in the flat area symmetrically about a pylon mounting axis that intersects said socket centering block perpendicular to said flat area, and a surrounding sidewall circumscribing said upper surface and said lower surface, said upper surface being concave about a principal focal axis that is both offset from said pylon mounting axis and acutely angled relative to said pylon mounting axis to impart a pre-determined flexion angle relative to said lower surface.

2. The socket centering block according to claim 1, wherein both said upper surface and lower surface define oval shapes.

3. The socket centering block according to claim 1, wherein said pre-determined flexion angle is within a range of from 2-20 degrees.

4. The socket centering block according to claim 3, wherein said pre-determined flexion angle is within a range of from 6-12 degrees.

5. The socket centering block according to claim 4, wherein said pre-determined flexion angle is 12 degrees.

6. The socket centering block according to claim 1, wherein said oval-shaped upper surface and lower surface are bounded by surrounding sides that converge lengthwise.

7. The socket centering block according to claim 1, wherein said concave upper surface conforms to the distal end of the residual limb and liner.

8. The socket centering block according to claim 7, wherein said concave upper surface seats the distal end of the residual limb and liner at an offset lengthwise along said upper surface toward one end thereof.

9. The socket centering block according to claim 1, wherein said upper surface is configured with a compound recess including as first section and a deeper second section centered at the midpoint of the first section.

10. The socket centering block according to claim 9, wherein said first section is substantially cylindrical defined by a flat floor and surrounding cylindrical walls.

11. The socket centering block according to claim 9, further comprising a slot in communication with said first recess section and opening outward through the sidewall.

12. The socket centering block according to claim 11, further comprising a bearing pin supported in said socket centering block at said slot.

13. The socket centering block according to claim 12, wherein said bearing in is suspended above said slot to serve as a roller.

14. The socket centering block according to claim 1, wherein said second surface is defined by four (4) bore holes formed symmetrically about the flat section of said lower surface to allow screw-attachment.

15. The socket centering block according to claim 14, further comprising a flat slide plate defined by four slots for passing corresponding screws into the bore holes.

16. In combination with a prosthetic leg including a hard socket for receiving a stump of a residual limb covered by a prosthetic liner, a foot attached beneath said socket, and a pylon between said socket and foot, said socket being defined by a unitary hard shell having a proximal open end, a primary volume, a distal end, and a chamber at said distal end defining a distal volume, an improvement comprising:

a socket centering block seated in the distal chamber of said socket for mounting and centering said socket to said prosthetic leg and establishing and maintaining a proper flexion angle and offset there between, said socket centering block further consisting of a solid member defined by an oval upper surface, oval lower surface having a flat area, and surrounding sidewall joining said upper surface and lower surface, a plane of said upper surface being inclined at a pre-determined flexion angle within a range of from 6-12 degrees relative to a plane of said lower surface, a recess formed in the upper surface of said socket centering block adapted for seating and centering a residual limb with a prosthetic liner, said recess having a principal focal axis, and a plurality of mounting holes formed in the flat area of said lower surface symmetrically about a pylon mounting axis that intersects said socket centering block perpendicular to said flat area, said pylon mounting axis being laterally offset from the axis of symmetry of said recess along said lower surface.

17. The socket centering block according to claim 15, wherein said recess is a compound recess in the top surface including a concave section to conform to the distal end of the residual limb and liner, and a deeper section centered at the midpoint of the concave section.

18. The socket centering block according to claim 17, wherein said deeper section is substantially cylindrical defined by a floor and surrounding cylindrical walls.

19. The socket centering block according to claim 18, further comprising a slot in communication with said deeper section opening outward through the sidewall.

* * * * *